(12) United States Patent
Tapia

(10) Patent No.: US 8,317,763 B2
(45) Date of Patent: Nov. 27, 2012

(54) SAFETY CAP FOR AN OSTOMY BAG

(76) Inventor: Larry Tapia, Temple Terrace, FL (US)

( * ) Notice: Subject to any disclaimer, the term of this patent is extended or adjusted under 35 U.S.C. 154(b) by 253 days.

(21) Appl. No.: 12/702,454

(22) Filed: Feb. 9, 2010

(65) Prior Publication Data

US 2011/0196322 A1  Aug. 11, 2011

(51) Int. Cl.
*A61F 5/44* (2006.01)
(52) U.S. Cl. ............ 604/332; 604/335; 138/89; 285/37; 285/407
(58) Field of Classification Search .................. 604/332, 604/335; 138/89; 285/37, 407
See application file for complete search history.

(56) References Cited

U.S. PATENT DOCUMENTS

| | | | | | |
|---|---|---|---|---|---|
| 1,836,336 A | * | 12/1931 | Replogle | ................. | 285/181 |
| 2,476,375 A | * | 7/1949 | Kent | ................. | 604/353 |
| 3,339,551 A | * | 9/1967 | Stoutenburgh | ................. | 604/349 |
| 3,357,430 A | * | 12/1967 | Rosenberg | ................. | 604/353 |
| 3,405,714 A | * | 10/1968 | Moss | ................. | 604/350 |
| 3,481,336 A | * | 12/1969 | Ipson | ................. | 604/342 |
| 3,507,282 A | * | 4/1970 | Burding | ................. | 604/333 |
| 3,604,424 A | * | 9/1971 | Windom | ................. | 604/350 |
| D232,086 S | * | 7/1974 | Graham | ................. | D24/129 |
| 3,827,107 A | * | 8/1974 | Moore | ................. | 24/16 R |
| 3,835,857 A | * | 9/1974 | Rogers et al. | ................. | 604/349 |
| 3,841,332 A | * | 10/1974 | Treacle | ................. | 604/335 |
| 3,881,486 A | * | 5/1975 | Fenton | ................. | 604/335 |
| 4,121,589 A | * | 10/1978 | McDonnell | ................. | 604/328 |
| 4,280,498 A | * | 7/1981 | Jensen | ................. | 604/335 |
| 4,300,560 A | * | 11/1981 | Steer et al. | ................. | 604/335 |
| 4,592,750 A | * | 6/1986 | Kay | ................. | 604/337 |
| 4,660,870 A | * | 4/1987 | Donley | ................. | 285/419 |
| 4,669,641 A | * | 6/1987 | Holmes | ................. | 222/543 |
| 4,693,712 A | * | 9/1987 | Bates | ................. | 604/323 |
| 4,713,067 A | * | 12/1987 | Rothenberg et al. | ................. | 604/353 |
| D295,220 S | * | 4/1988 | Kay | ................. | D24/129 |
| 4,864,698 A | * | 9/1989 | Brame | ................. | 24/442 |
| 4,930,543 A | * | 6/1990 | Zuiches | ................. | 138/110 |
| D326,155 S | * | 5/1992 | Boehringer et al. | ................. | D24/129 |
| 5,193,553 A | * | 3/1993 | Kalinoski | ................. | 600/580 |
| 5,348,048 A | * | 9/1994 | Schirado et al. | ................. | 137/588 |
| 5,505,500 A | * | 4/1996 | Webb et al. | ................. | 285/223 |
| 5,624,410 A | * | 4/1997 | Tsukada et al. | ................. | 604/256 |
| 5,657,792 A | * | 8/1997 | Prest | ................. | 138/89 |
| 5,827,249 A | * | 10/1998 | Jensen | ................. | 604/349 |
| 5,855,206 A | * | 1/1999 | Ireland | ................. | 128/844 |
| 5,870,849 A | * | 2/1999 | Colson, Jr. | ................. | 43/25.2 |
| 5,879,029 A | * | 3/1999 | Wilks | ................. | 285/8 |
| 6,007,525 A | * | 12/1999 | Martell | ................. | 604/333 |
| 6,033,390 A | * | 3/2000 | von Dyck | ................. | 604/332 |
| 6,156,140 A | * | 12/2000 | Ayres | ................. | 156/66 |
| 6,248,096 B1 | * | 6/2001 | Dwork et al. | ................. | 604/349 |
| 6,419,664 B1 | * | 7/2002 | von Bulow et al. | ................. | 604/337 |

(Continued)

*Primary Examiner* — Tatyana Zalukaeva
*Assistant Examiner* — Ginger T Chapman
(74) *Attorney, Agent, or Firm* — Jerry Haynes; Law Office of Jerry D. Haynes, P.A.

(57) ABSTRACT

A safety cap assembly for sealing an ostomy bag opening comprising: an attachment means, where said attachment means secures the safety cap assembly to the ostomy bag opening; a vertical tubing, where the vertical tubing fits onto the ostomy bag opening; an absorption barrier, where said barrier lies within the inner portion of the vertical tubing; and an end cap, said end cap encloses and seals the tubing. In one exemplary embodiment, the attachment means includes a Velcro fastening strip. The absorption barrier may be made of a cotton material or other absorbent material.

5 Claims, 1 Drawing Sheet

U.S. PATENT DOCUMENTS

| | | | |
|---|---|---|---|
| 6,849,066 B1 * | 2/2005 | Ciok et al. | 604/332 |
| 7,044,939 B1 * | 5/2006 | Fajnszajn | 604/349 |
| 7,517,340 B2 * | 4/2009 | Barrientos | 604/353 |
| 7,896,857 B2 * | 3/2011 | Kay et al. | 604/317 |
| 7,947,025 B2 * | 5/2011 | Buglino et al. | 604/335 |
| 8,088,114 B1 * | 1/2012 | Pauze | 604/335 |
| 2005/0134037 A1 * | 6/2005 | Bruno et al. | 285/7 |
| 2009/0209926 A1 * | 8/2009 | Cochran | 604/332 |
| 2010/0211033 A1 * | 8/2010 | Blum | 604/335 |
| 2011/0282311 A1 * | 11/2011 | Nishtala | 604/332 |

* cited by examiner

SAFETY CAP FOR AN OSTOMY BAG

FIELD OF INVENTION

The present invention relates to a cap for insertion onto an ostomy bag to prevent leakage.

DESCRIPTION OF RELATED ART

An ostomy pouch system provides a means for the collection of waste from a biological system such as the colon, urinary tract or ileum from a patient who medical condition necessitates use of such. The ostomy systems usually include a mounting base plate and a pouch attached thereto. The pouch receives the waste materials and provides a means to dispose of the materials. In application, the pouch may be disposable where the pouch is disposed of entirely along with the waste materials within the pouch or reusable where the waste materials may be released through a pouch opening.

In the case of a reusable pouch, a bottom opening permits the contents to be emptied while the pouch remains in place on the patient's body. The reusable pouches use various types of closure means that seal the bottom opening while the pouch collects discharged waste from the patient. Clamps and other devices are used to seal the opening to ensure that leakage does not take place while the pouch is in use. Although the clamps and caps used on the ostomy bags are somewhat effective, inevitably a leakage does occur and may appear on a patient's skin or clothing.

U.S. Pat. No. 4,983,172 discloses a hinge clip with two limbs that is used as a closure for a drainage ostomy pouch. Such types of clips are commonly used for pouches, however where a pouch includes a tubing opening such a clamp may be ineffective. An effective sealing means is needed to secure the tube opening of an ostomy bag and therefore to prevent leakage.

SUMMARY OF THE INVENTION

The present invention relates to a safety cap assembly for sealing an ostomy bag opening comprising: an attachment means, where said attachment means secures the safety cap assembly to the ostomy bag opening; a vertical tubing, where the vertical tubing fits onto the ostomy bag opening; an absorption barrier, where said barrier lies within the inner portion of the vertical tubing; and an end cap, said end cap encloses and seals the tubing. In one exemplary embodiment, the attachment means includes a Velcro fastening strip. The absorption barrier may be made of a cotton material or other absorbent material.

DETAILED DESCRIPTION

The present invention relates to a safety cap that is placed on the opening of an ostomy bag and provides an effective seal of the opening to prevent leakage. The safety cap according to the present invention securely attaches to the drain tube of an ostomy bag and therefore creates a sealed barrier to prevent the leakage. The safety cap according to the present invention includes a cotton absorbent layer just inside the end cap that provides an absorption material to help absorb any secure the seal on the ostomy bag opening.

Figure 1:
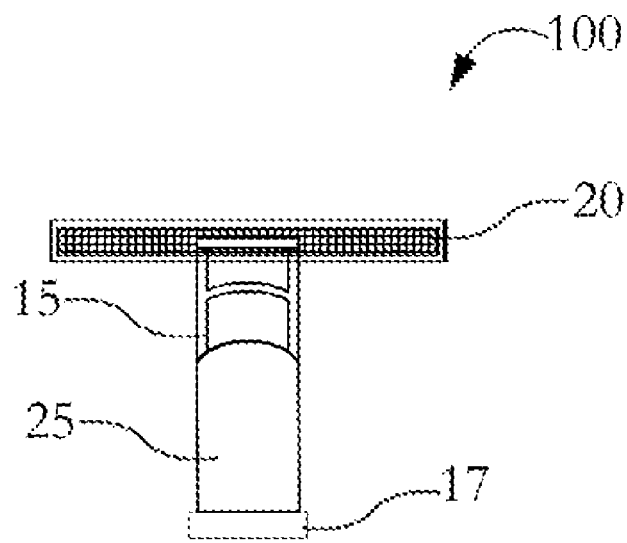
FIG. 1 depicts a safety cap for ostomy bag in accordance with the present invention.

FIG. 1 depicts a Safety Cap Assembly 100 in accordance with the present invention.

The Safety Cap Assembly 100 includes a Velcro® Fastening Strip 20 commonly known as a hook and loop fastening strip, which provides an attachment means for the Safety Cap 100. The Vinyl Tubing 15 includes a top end and a bottom end, where the attachment means or Strip 20 is attached to the top end and an opening is provided at the bottom end. An End Cap 17 provides a means to seal the opening at the bottom end of the Vinyl Tubing 15. In one particular embodiment, the End Cap 17 snaps into place to seal the opening. The Vinyl Tubing 15 includes an Absorption Barrier 25 just inside of the End Cap 17. The Absorption Barrier 25 within the Vinyl Tubing 15 provides a means for absorbing liquid or semi-liquid waste before it reaches the End Cap 17. In one exemplary embodiment, the Absorption Barrier 25 may be made of cotton material, however other comparable absorbent materials may be utilized such as non-woven fabrics. The top end of the Vinyl Tubing 15 securely fits over an opening of an ostomy bag and may be sealed into place by wrapping the Velcro® Fastening Strip 20 around the outside of the Vinyl Tubing 15. In one particular embodiment of the present invention, the Vinyl Tubing 15 includes a ¾ inch outer diameter and a ⅝ inch inner diameter.

Figure 2:
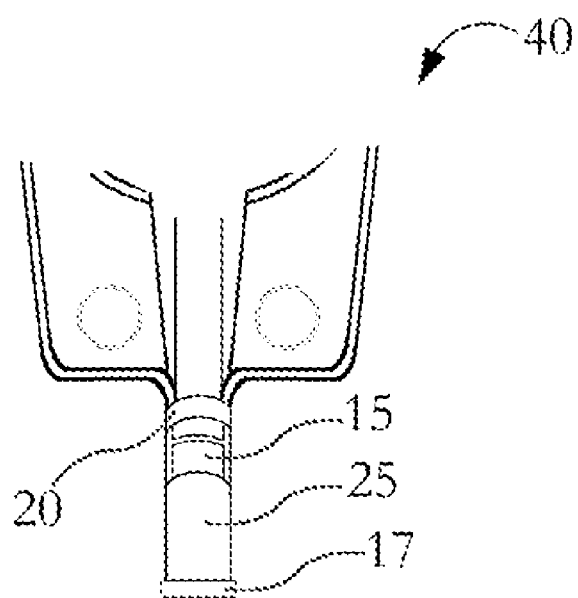
FIG. 2 depicts the attachment of the safety cap according to the present invention onto an ostomy bag.

FIG. 2 depicts the application of the Safety Cap Assembly 100 in accordance with the present invention. An Ostomy Bag 40 is provided with a Safety Cap Assembly 100 in accordance with the present invention. As depicted, the Vinyl Tubing 15 fits onto the opening of the Ostomy Bag 40 and is secured with the Velcro® Fastening Strip 20. Once in place this Safety Cap Assembly 100 provides a secure and effective means to prevent leakage from the Ostomy Bag 40. Use of the Safety Cap Assembly 100 reduces the risk of leakage and helps to prevent the spillage of waste from a patient's skin or clothing. The Safety Cap Assembly 100 provides a more effective seal of the ostomy bag opening as opposed to a clamp or other closure means used in the prior art.

The Tubing 15 includes the highly effective Absorption Barrier 25 that helps to absorb liquid moisture in order to prevent and reduce the likelihood of leakage from the ostomy bag opening. The Safety Cap Assembly 100 is a disposable device that is attached to the ostomy bag opening with relative ease by using the Velcro® Fastening Strip 20. Use of the Safety Cap Assembly 100 therefore minimizes bacterial infections and other hazards that may be created due to a leaking ostomy bag. The instant invention has been shown and described in what it considers to be the most practical and preferred embodiments. It is recognized, however, that departures may be made there from within the scope of the invention and that obvious modifications will occur to a person skilled in the art.

What is claimed is:

1. A safety cap assembly for sealing an ostomy bag opening comprising:
   a. an attachment means, where said attachment means secures the safety cap assembly to the ostomy bag opening, where said attachment means is a hook and loop fastening strip;
   b. a vertical tubing, where the vertical tubing fits onto the ostomy bag opening;
   c. an absorption barrier, where said barrier lies within an inner portion of the vertical tubing to absorb liquids from the ostomy bag; and
   d. an end cap, said end cap encloses and seals the tubing.

2. The safety cap assembly according to claim 1, where the absorption barrier is made of a cotton material.

3. A safety cap assembly for sealing an ostomy bag opening comprising:
   a. a vertical tubing, where the vertical tubing includes a top end and a bottom end where the top end fits onto the ostomy bag opening, and where the vertical tubing includes a ¾ inch outer diameter and a ⅝ inch inner diameter;
   b. a hook and loop fastening strip, where said hook and loop fastening strip is attached to the top end of the tubing and secures the safety cap assembly to the ostomy bag opening;
   c. an absorption barrier, where said barrier lies within an inner portion of the vertical tubing to absorb any liquid from the ostomy bag, and where the absorption barrier is made from a cotton material; and
   d. an end cap, said end cap encloses and seals the by snapping place.

4. The safety cap assembly according to claim 1, wherein said absorption barrier is made from a non-woven fabric.

5. The safety cap assembly according to claim 1, wherein the vertical tubing includes a ¾ inch outer diameter and a ⅝ inch inner diameter.

* * * * *